United States Patent [19]
Jensen

[11] Patent Number: 5,928,254
[45] Date of Patent: Jul. 27, 1999

[54] TONGUE CLEANING DEVICE

[76] Inventor: Fred R. Jensen, 11432 Carlile St., Northglenn, Colo. 80233

[21] Appl. No.: 08/896,583

[22] Filed: Jul. 18, 1997

[51] Int. Cl.⁶ .................................................. A61B 17/00
[52] U.S. Cl. ............................................................ 606/161
[58] Field of Search ..................................... 606/160–162

[56] References Cited

U.S. PATENT DOCUMENTS

| | | |
|---|---|---|
| D. 118,318 | 12/1939 | Fortunati . |
| D. 265,506 | 7/1982 | Finamore . |
| 717,456 | 12/1902 | Schiel . |
| 1,533,123 | 4/1925 | Lewis . |
| 1,746,877 | 2/1930 | Tompkins . |
| 1,811,775 | 6/1931 | Barkwill . |
| 1,851,396 | 3/1932 | Mabry . |
| 2,049,956 | 8/1936 | Greeenberg . |
| 2,405,029 | 7/1946 | Gallanty et al. . |
| 2,583,750 | 1/1952 | Runnels . |
| 2,651,068 | 9/1953 | Seko . |
| 2,677,843 | 5/1954 | Goodman . |
| 2,723,661 | 11/1955 | Hull . |
| 3,178,747 | 4/1965 | Peterson . |
| 3,811,447 | 5/1974 | Weber ...................................... 606/181 |
| 3,890,964 | 6/1975 | Castandeo . |
| 5,061,272 | 10/1991 | Reese . |

FOREIGN PATENT DOCUMENTS 0537979  6/1922  France .................................... 606/161

*Primary Examiner*—Michael Buiz
*Assistant Examiner*—William W. Lewis
*Attorney, Agent, or Firm*—Lee G. Meyer

[57] ABSTRACT

A hand held tongue cleaning device for applying the correct "downward" pressure on the tongue surface to release entrapped material without damaging the tongue. The device has a flat, curved cleaning element consisting of at least one blunted blade for cleaning the tongue on one end; and, a flat, curved handle on the other to form an elongated 'S' profile. The curved blunted blade element is adapted for moving over the surface area of the tongue to dislodge the surface material from the tongue and withdraw the accumulated substance even from the back recesses of the mouth without injury to the tongue or triggering the "gag reflex".

9 Claims, 1 Drawing Sheet

TONGUE CLEANING DEVICE

BACKGROUND OF THE INVENTION

1. Field of the Invention

This invention relates to tongue-cleaning devices and more particularly to devices which will enable the user to quickly and easily clean the tongue without causing injury to delicate membranes or triggering the "gag reflex".

2. Description of Related Art

Oral hygiene has become of increasing world wide concern, especially among teenagers and older adults. Many dentifrices, flosses, toothpastes, toothbrushes and other articles for maintaining oral hygiene have been developed and sold in recent years. It is generally recognized that in many cases, complete oral hygiene must include the removal of surface material from the tongue, including the back of the tongue in the rearward recesses of the mouth and throat.

In the past, tongue-cleaning devices generally have been of two kinds: tongue "scrapers"; and tongue brushes. The scraper has usually comprised a curved scraping element mounted on a handle, for example U.S. Pat. No. 1,533,123, or a straight scraper resembling a miniature hoe mounted at right angles to the handle, for example U.S. Pat. No. 1,851,396. These scrapers, have been objectionable for a number of reasons, chief of which is the very real possibility of injuring the delicate mucous membranes forming the tongue surface. In order to perform the operation with any measure of success, relatively sharp edges were required, which frequently produced cuts or abrasions of the membranes. If the edges were sufficiently dulled to eliminate this danger, the device was not capable of removing the deposits on the tongue surface, since these deposits cling to the tongue surface, and particularly to the many interstices within the tongue's roughened surface. Moreover, devices of this general character were entirely incapable of removing the secretions in these minute interstices, and especially at the back of the tongue.

One reason for this deficiency was the shape of the prior art devices. Specifically, they did not incorporate a design that allowed proper manipulation of the working surface to get the correct leverage on the device and to provide the deft manipulation required at the back of the tongue to prevent gagging.

The second type of tongue-cleaning device, the brush, overcame some of the forgoing objections by use of soft bristles, but such soft bristles did a poor cleaning job. The nature of deposits on the tongue is such as to be relatively incapable of removal by brushing. If hard bristles are used, the surface of the tongue is penetrated causing the rupture of blood vessels, and thus, the danger of infection. Moreover, brushes do not carry residue out of the mouth, but allow part or even most of it to travel to the stomach.

Many people do not employ a separate tongue cleaning device at all. They simply use a toothbrush to scrub or otherwise scour the tongue surface in an attempt to remove surface material. This is generally ineffective and is particularly ineffective if the person is, for example, a smoker or tends to eat highly seasoned foods. The main problem associated with scrubbing the tongue with a tooth brush is that the tongue is a muscle with a rough surface somewhat similar to the layering of scales on a fish. While brushing moves these "scales" around, the fact is that brushing alone is relatively ineffective in removing matter that is lodged or otherwise retained under the surface of this rough textured skin.

Because of this layering, one must actually "scrape" or "milk" the tongue surface in order to dislodge and free material trapped on or just beneath the tongue's surface. Additionally, the majority of the material which must be removed is at the back recesses of the mouth and throat, next to the tissue which triggers the "gag reflex." It is that part of the tongue which is most difficult to clean and is virtually impossible to brush.

Thus it would be advantageous to have a device which is inexpensive, easy to use, gives positive results, and reaches the back recesses of the tongue area without triggering the gag reflex. Further, it would be advantageous to have a light weight, yet durable device that could be carried in a purse or pocket for use other than in the home. Finally, it would be advantageous to have a device that is functionally designed to allow the user to deftly manipulate the cleaning device to remove trapped material without damaging the tongue membrane from either side of the users mouth using either hand.

A number of prior art devices attempt to solve the hygiene problem, without success. For example, U.S. Pat. No. 3,477,435 discloses a tongue scraper comprising two curved surfaces joined at right angles. This device, however, does not incorporate a means for exerting downward pressure on the device, and incorporates a separately formed handle joined to the scraper, which adds to manufacturing expense. U.S. Pat. No. 1,891,864 also discloses a tongue scraper comprising a flat edge.

U.S. Pat. No. 1,533,123 discloses a tongue scraper comprising a curved, slightly concave surface with a straight, flat handle. While the curve generally conforms to the shape of the tongue, the handle does not afford the manipulative ability required.

U.S. Pat. No. D95,777 discloses a toothbrush having a spoon•shaped member at one end, presumably for scraping the tongue. It is less than fully affective for cleaning the tongue surface. U.S. Pat. Nos. 2,049,956; 2,708,762 and 4,356,585 also disclose toothbrushes having a scraper at one end. In each case, however, the tongue scraper is less than fully effective for cleaning the back recesses of the tongue.

U.S. Pat. No. 4,455,704 discloses yet another combined toothbrush and tongue scraper. However, because of the manner in which the tongue scraper extends from the toothbrush handle, holding the brush for scraping the tongue is awkward. A somewhat similar tongue scraper is disclosed in U.S. Pat. No. 1,811,775. Another combined toothbrush and tongue cleaner, wherein the tongue cleaner comprises a curved member at the end of the handle, is disclosed in U.S. Pat. No. 1,860,924. The curved portion is not, however, wide enough to conform to the shape of the tongue and is therefore less than fully effective.

U.S. Pat. No. D 118,318 discloses a tongue scraper in the form of a loop, as does U.S. Pat. No. 4,488,327. These tongue scrapers will not conform well to the upper surface of the tongue. U.S. Pat. Nos. 3,683,924, 3,697,366 and 3,811,447 disclose generally U-shaped flexible scrapers. While these scrapers, because of their flexibility, can be formed to the shape of the surface of the tongue, they require two hands to use, and do not afford the manipulation required for cleaning the back of the tongue. Still other scrapers, each of which suffers from one or more of the aforementioned drawbacks, are disclosed in U.S. Pat. Nos. 1,658,706; 1,741,143; 2,405,029; 2,583,750 and 3,890,964. Various of the tongue cleaners referenced above are uncomfortable to grasp or cannot be easily manipulated; some require a number of parts and are relatively expensive to manufacture.

In addition there are numerous scrapers and tools for removing surface matter from objects other than the human tongue. For example, U.S. Pat. No. 3,178,747 teaches a culinary scraper that, in operation, is used in an inverted manner. U.S. Pat. No. 1,746,877 shows a concave scraping cleaner for treating the skin. U.S. Pat. No. 717,456 shows a flat scraper with a hook on the end.

It would therefore be advantageous to provide an improved tongue cleaner which is effective for cleaning the surface of the tongue and is formed from a minimum number of parts for reducing manufacturing costs, which embodies a grip or handle which can be comfortably grasped by both right and left handed users and allows leverage and manipulation of the cleaner device to facilitate the removal of retained material without injuring the tongue or gagging the user.

SUMMARY OF THE INVENTION

There is provided an inexpensive to manufacture, efficient device for cleaning the tongue from either side of the mouth, which is suitable for grasping by both right and left handed users. According to the invention, a device is provided for removing surface matter from the human tongue; more particularly, an inexpensive, cleanable, portable, hand held device for applying the correct "downward" pressure on the tongue surface to release entrapped material without damaging the tongue is provided. The present invention envisions a tongue-leaning device which, by virtue of its construction and ease of cleaning, is sanitary, may be readily washed or sterilized, and may be used safely without any danger of depositing germs on the tongue or causing infection.

It has now been discovered that the disadvantages of the prior art can be overcome with a device having a curved working surface or cleaning blade on one end and a gripping surface having a curvature, reversed from that of the working surface, on the other end to form a cleaning tool having an elongated 'S' profile. The major length of the device is preferably straight with curves in opposite directions at either end. Preferably, the tongue cleaning device of the instant invention comprises a curved blade element having at least one blunted cleaning edge, adapted for moving over the surface area of the tongue to dislodge the surface material from the tongue and withdraw the accumulated substance, even from the portion of the tongue located in the back recesses of the mouth into the throat, without injury to the tongue or triggering the "gag reflex".

The device of the present invention contains a curved blade cleaning element having at least one blunted edge for contacting the tongue; and, a handle member of a curved terminal portion adapted for gripping, wherein the blade element and the terminal portion are curved in opposite directions, one from the other, to form an elongated "s" shaped device.

In one embodiment, the tongue cleaner in accordance with the invention comprises a curved handle and a curved cleaning element portion secured at one end to the handle. In a preferred embodiment, the cleaning portion is curved in general conformity with a human tongue and has a substantially semicircular cross section defining a faint concave channel on the inwardly curving surface of the cleaning element for re-accumulating matter removed from the tongue. In a preferred embodiment the curved grip and cleaning element are integrally formed and the handle has a flattened cross section and a generally arc-shaped contour forming a curved surface. By turning the cleaning device over, the curved surface of the handle switches, as gripping surfaces for the thumb and other fingers of the users other hand, thus allowing cleaning from either side of the mouth. In this configuration the curved cleaning element carries two substantially identical blunted cleaning edges, disposed on opposite sides of the cleaning element, such that the device can be rotated about 180 degrees to apply the opposite blunted edge to the tongue surface for cleaning from the other side of the mouth.

Further features and advantages of the tongue cleaner in accordance with the present invention will be more fully apparent from the following detailed description and annexed drawings of the presently preferred embodiment thereof, which form part of the specification.

DESCRIPTION OF THE PREFERRED EMBODIMENTS

Figure 1:
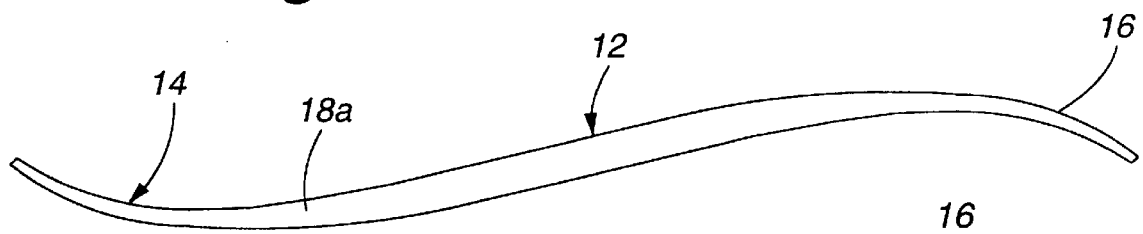
FIG. 1 is a top view of the device illustrating the functional shape of a preferred device embodying the principles of the invention.

Turning to FIG. 1, there is shown the device 10 of the instant invention having a generally "S" shaped configuration with a straightened body portion 12, a curved cleaning element 14, having disposed on either edge thereof blunted cleaning surfaces 18a and 18b, and a curved handle or gripping portion 16. As shown, the tongue scraper 10 is integrally formed, preferably from a strip of molded plastic. On the device 10, which is preferably about 6 inches in length, the curved deviation on the handle portion 16 and the cleaning element 14 are approximately equal so that the device forms an elongated "S". It will be realized that the curvature can be deviated to accommodate different anatomies, such as adolescent tongues or the like. As better seen in FIG. 2, in one embodiment the cleaning element 14 may have more of a curvature than the handle portion 16 to allow access to the inner reaches and recesses of the mouth and throat to reach the back of the tongue without triggering the gag reflex. In one embodiment (not shown), primarily for adolescent tongues, the curvature of the cleaning element is substantially more than the handle portion.

Figure 3:
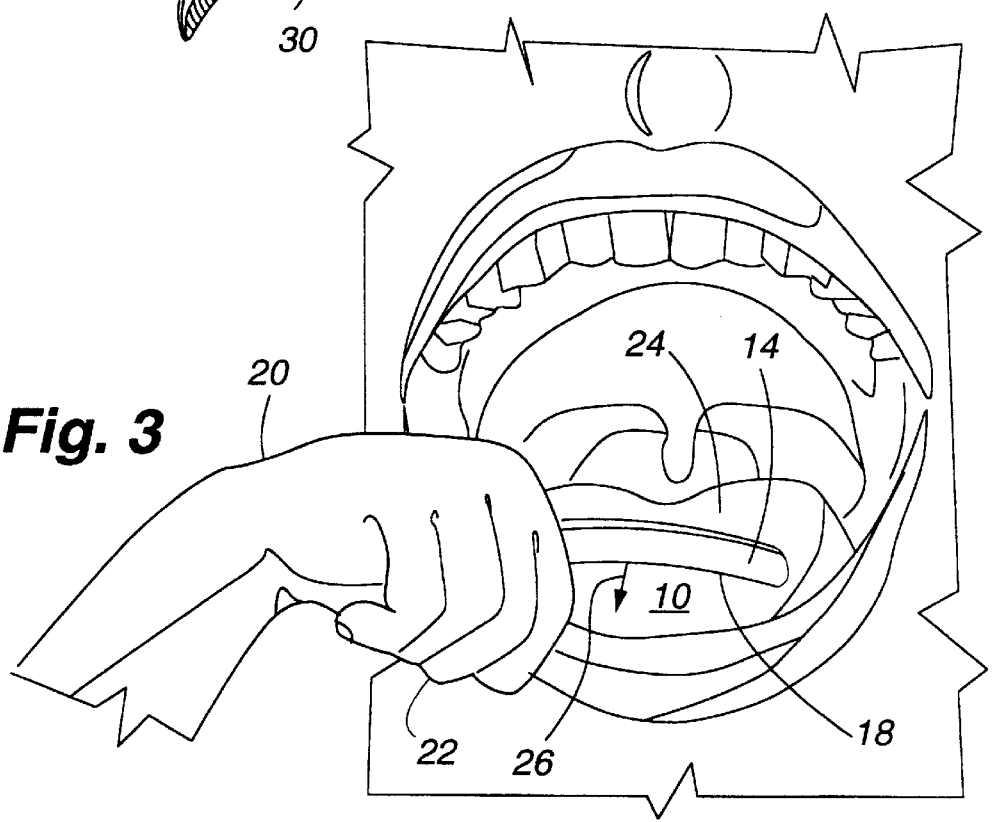
FIG. 3 is an illustration of the device in use in the human mouth.

As better seen in FIG. 3, in operation the user grasps the device 10 in his hand 20 using the pressure of the opposing thumb (not visible) in contact with the flattened portion of the handle(not visible), and wraps the fingers 22 of the hand about the forward flattened portion so that device 10 is able to be manipulated by pressure from the thumb and twisting of the hand to provide a positive pressure on the tongue surface 24. The cleaning element 14 of the device 10 containing the beveled blade surface 18a in the "tongue down" position, is placed on the back recesses of the tongue 24 as shown.

In operation the device 10 is placed squarely on the surface of the tongue 24 and, with downward pressure, urged toward the front of the mouth in the direction of arrow 26 to manipulate the material on the surface of the tongue forward and gently urge the retained material from the interstices of the tongue without damaging the tongue surface, but "milking" the interstices with a downward pressure of the constantly moving beveled blade surface 18a of the cleaning element 14 of the device 10.

Thus, when the beveled blade surface 18a (or 18b) of the curved cleaning element is pressed gently into engagement with the tongue surface and moved toward the tip of the tongue, the adjacent portion of the tongue surface moves into engagement with the device to expel foreign material and then move the dislodged material along the surface of the tongue ahead of the cleaning element throughout the length of the tongue. When the pressure is slightly relaxed, the accumulated substance adheres to the blade or cleaning portion of the device for removal from the mouth. After a few gentle strokes over the tongue surface, placing the cleaning element under a spray of water will remove the accumulation, and leave the tongue surface clean.

The device may be molded of any suitable resilient material and preferably one of "plastic" because of the ease of cleaning these materials. The shape of the terminal portion or grip embodies a curvature inverse from the blade with the curvature displacement of both ends being preferably less than the width of the tongue. It is greatly preferred to have the terminal portion or handle generally curved throughout its length, such that the opposing thumb and the fingers grip the device to allow maximum control of the blade. The curved handle embodiment allows use in either hand. Likewise, the beveled blade portion of the curved cleaning element is configured so that either beveled blade surface of the cleaning element can be used to clean the tongue, allowing use from either side of the mouth.

Figure 2:
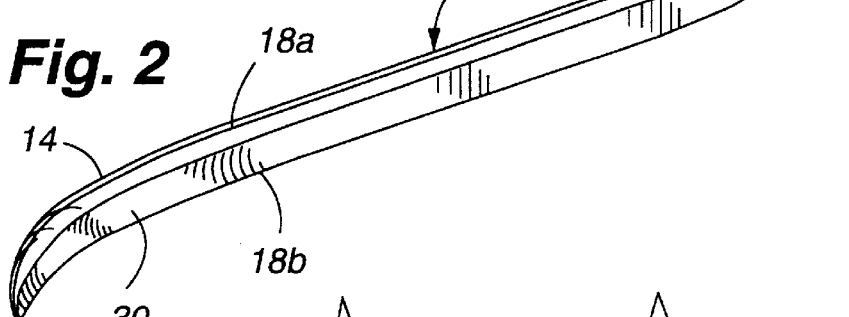
FIG. 2 is a canted side view illustrating the gripping and cleaning features of the invention.

In accordance with the embodiment shown in FIG. 2, cleaning element 14 is curved and has a generally semicircular cross section defining a convex channel 30. In operation the channel 30 provides a receptacle for matter removed from the tongue surface. To use the scraper 10, the scraper is grasped by the handle portion 16, preferably with the thumb along the straightened body portion 12 in the vicinity of the junction between the body portion 12 and the cleaning element 14, and with the other fingers wrapped about the curved surface 16. Because of the design of the scraper 10, it will be apparent that the scraper may be gripped in the foregoing fashion regardless of whether the user is right or left handed. With the scraper 10 thus grasped, the blade 18a or 18b, depending on whether the scraper is held in the left or right hand, of the cleaning element 14 is applied to the upper surface at the back of the tongue with the channel 30 angled downward toward the tongue surface in the fashion of a road grader blade. As the upper surface of the tongue is curved, holding the scraper 10 in this fashion results in one of the beveled blades 18a or 18b contacting the upper surface of the tongue substantially along its entire width.

At this point, the scraper is moved forward such that the surface 18a or 18b of cleaning element contacts the upper surface of the tongue for removing odor-causing and other objectionable matter, with any such matter accumulating in the channel 30. Due to its semicircular shape, the channel 30 retains the accumulated matter and prevents it from dripping back onto the tongue as the cleaning progresses. The cleaning device 10 may then be rinsed out by hand or in a dishwasher, whereupon it is again ready for use. From the foregoing, it will be apparent that the tongue cleaner in accordance with the present invention is inexpensive to manufacture, extremely effective, and suitable for grasping by both right and left hand users.

While I have herein shown and described a preferred embodiment of the scraper of the present invention, it will be apparent to those of ordinary skill in the art that still further changes and modifications may be made therein without departing from the spirit and scope of the invention. Accordingly, the above description should be construed as illustrative and not in a limiting sense, the scope of the invention being defined by the following claims. While one illustrative preferred embodiment of this invention has been shown and described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. Thus, it should be understood that this invention is not to be limited to the exact forms disclosed and many changes in detail and construction of the invention may be made without departing from the spirit thereof.

I claim:

1. A tongue cleaner comprising:
   a curved cleaning element having at least one blunted blade-like edge for contacting the tongue and a generally semicircular cross section to form a channel in said cleaning element said channel extending from edge to edge of said curved cleaning element,
   a handle member of a curved terminal portion adapted for gripping, wherein the cleaning element and the terminal portion are curved in opposite directions, one from the other, to form an elongated "S" shaped device.

2. The tongue cleaner according to claim 1, wherein said cleaning element has a pair of blunted blade-like edges for contacting the tongue disposed on either edge of said cleaning element.

3. The tongue cleaner according to claim 1, wherein said at least one blunted blade-like edge runs substantially the length of the edge of said cleaning element.

4. A tongue cleaner for removing contained material on the surface of a tongue comprising: an integrally formed, substantially rigid member defining a curved handle portion and a curved cleaning element, said handle portion and cleaning element being of substantially equal width and curved in opposite directions to form an elongated "s" configuration, said cleaning element being curved in general conformity with a human tongue and having at least one blunted blade portion running substantially the edge of said cleaning element and having an arc-shaped cross section defining a first concave channel, said channel extending from edge to edge on the inward curved portion of said cleaning element adapted to reaccumulate material removed from the tongue surface; said handle also having a generally arc-shaped flat cross section for forming a gripping surface for the thumb and other fingers, and being adapted for use by either the right or left hand.

5. The tongue cleaner according to claim 4, wherein said cleaning element has a pair of blunted blade-like edges for contacting the tongue disposed on either edge of said cleaning element and wherein said at least one blunted blade-like edge runs substantially the length of the edge of said cleaning element.

6. A method for cleaning a tongue comprising:
   gripping an elongated handle portionof a device having a curved shape adapted for gripping by hand; and,
   moving a cleaning element having a curved shape, in reverse of said handle curved shape, wherein the cleaning element has at least one blade surface on the edge of said cleaning element adapted for contacting the surface of said tongue along said tongue to remove material retained on said tongue.

7. The method for cleaning a tongue according to claim 6, wherein said cleaning element has a pair of blunted blade-like edges for contacting the tongue disposed on either edge of said cleaning element.

8. A method for cleaning a tongue comprising:

gripping an elongated handle portion of a device having a curved shape adapted for gripping by hand; and, moving a cleaning element having a curved shape, in reverse of said handle curved shape, wherein the cleaning element has at least one blade surface on the edge of said cleaning element adapted for contacting the surface of said tongue along said tongue to remove material retained on said tongue, wherein said at least one blunted blade-like edge runs substantially the length of the edge of said cleaning element.

9. The method for cleaning a tongue according to claim 6, wherein said cleaning element has a generally semicircular cross section to form a channel therein.

* * * * *